US008808160B2

(12) United States Patent
Davis

(10) Patent No.: US 8,808,160 B2
(45) Date of Patent: Aug. 19, 2014

(54) METHOD AND APPARATUS FOR PROVIDING THERAPY USING SPONTANEOUS OTOACOUSTIC EMISSION ANALYSIS

(76) Inventor: Dorinne S. Davis, Mt. Arlington, NJ (US)

( * ) Notice: Subject to any disclaimer, the term of this patent is extended or adjusted under 35 U.S.C. 154(b) by 304 days.

(21) Appl. No.: 13/029,340

(22) Filed: Feb. 17, 2011

(65) Prior Publication Data

US 2011/0207991 A1     Aug. 25, 2011

Related U.S. Application Data

(60) Provisional application No. 61/338,508, filed on Feb. 19, 2010.

(51) Int. Cl.
*H04R 25/00*     (2006.01)
*A61M 21/00*     (2006.01)

(52) U.S. Cl.
USPC ............................................. 600/28; 600/25

(58) Field of Classification Search
USPC .......... 600/25–28; 607/56, 57, 137; 381/23.1, 381/60, 312, 328; 623/10
See application file for complete search history.

(56) References Cited

U.S. PATENT DOCUMENTS

| 4,156,116 | A | * | 5/1979 | Yanick | 381/317 |
|---|---|---|---|---|---|
| 5,776,179 | A | * | 7/1998 | Ren et al. | 607/137 |
| 6,342,035 | B1 | * | 1/2002 | Kroll et al. | 600/25 |
| 6,674,862 | B1 | * | 1/2004 | Magilen | 381/60 |
| 2006/0222195 | A1 | * | 10/2006 | Bramslow | 381/318 |
| 2009/0124850 | A1 | * | 5/2009 | Moore et al. | 600/28 |
| 2010/0183161 | A1 | * | 7/2010 | Boretzki | 381/60 |
| 2011/0071340 | A1 | * | 3/2011 | McGuire | 600/28 |

OTHER PUBLICATIONS

G.R. Long, C.L. Talmadge, "Spontaneous otoacoustic emission frequency is modulated by heartbeat," J. Acoust. Soc. Am. 102 (5), Nov. 1997, pp. 2831-248.*
Dorinne S. Davis-Kalugin, Davis Addendum to the "Tomatis Effect", 148th Meeting of the Acoustical Society of America, Nov. 15-19, 2004, pp. 1-7, San Diego.

* cited by examiner

*Primary Examiner* — Jacqueline Cheng
*Assistant Examiner* — Eileen Foley
(74) *Attorney, Agent, or Firm* — Moser Taboada

(57) ABSTRACT

A method and apparatus for providing therapy using spontaneous otoacoustic emission (SOAE) analysis is described. In one embodiments, a method for utilizing the voice-ear-brain connection to achieve self-healing includes capturing audio emissions of at least one ear of a patient, determining a frequency spectrum of the audio emissions, identifying a peak frequency in the frequency spectrum, and producing at least one audio signal in response the peak frequency.

18 Claims, 3 Drawing Sheets

METHOD AND APPARATUS FOR PROVIDING THERAPY USING SPONTANEOUS OTOACOUSTIC EMISSION ANALYSIS

CROSS-REFERENCE TO RELATED APPLICATIONS

This application claims priority to U.S. Provisional Patent Application Ser. No. 61/338,508, filed Feb. 19, 2010, which is incorporated by reference herein in its entirety.

BACKGROUND

1. Technical Field

The embodiments of the present invention generally relate to bioacoustic therapeutic techniques and, more specifically, to a method and apparatus for providing therapy using spontaneous otoacoustic emission (SOAE) analysis.

2. Description of the Related Art

Spontaneous otoacoustic emissions (SOAEs) are sounds (i.e. audio signals) emitted from the ear. More specifically, SOAEs are continuous narrowband frequency specific audio signals. The actual location of the emission is still questionable, but most researchers in the field consider the sound to be emitted from the Outer Hair Cells of the cochlea in the inner ear. Some researchers suggest that neural signals from the inferior colliculus in the mid brain are sent to the motor cells in the cochlea which are important for response to frequency specific tones or pitches. The study of SOAEs involves understanding the neurophysiological and anatomical basis of sound production and detection as well as understanding the nature of acoustic signal propagation through an elastic medium. Because the SOAEs are produced in the ear, after traveling outwardly through the ear they can be captured for analysis.

Until recently, most researchers have evaluated SOAEs as a connection with the hearing or auditory system of the body, such as neonatal hearing screenings. More recently, SOAEs have been explored for other possible uses. For example, SOAEs have been explored as a potential physiological biometric, where SOAEs have been considered for use as a biometric signature to be used as a potential computer password and/or cellphone personal identifier.

Prior to this recent application of SOAEs as a biometric, there is little research reported regarding why humans produce SOAEs. In 2004, DS Davis, at the Acoustical Society of America conference in San Diego, Calif., presented The Davis Addendum to the 'Tomatis Effect' (Davis-Kalugin, D S. *The Davis Addendum to the 'Tomatis Effect'*. 148th Meeting of the Acoustical Society of America, Nov. 15-19, 2004, San Diego #2pSC14). This presentation connected the irregular patterns identified from SOAEs with the irregular frequency patterns identified through vocal analysis and found 100% correlation between the sounds emitted from the ear and the sounds emitted by the voice. This presentation built upon the initial three laws established in 1957 known as The Tomatis Effect, which suggested that the voice produces what the ear hears and when the correcting frequencies are reintroduced to the ear, the voice regains coherence. The Davis Addendum to The Tomatis Effect proposed two additional laws suggesting that not only does the voice produce what the ear hears, but that the ear emits the same stressed frequencies as the voice and, when the correcting frequencies are reintroduced, the voice and ear regain coherence. Collectively these five laws are now known as The Voice-Ear-Brain Connection, a newly identified subtle energy system supporting the concept: when the voice and ear are in balance as indicated by their audio emissions, the brain supports balancing the body with self-healing.

Although the Voice-Ear-Brain Connection is an important concept, there is a need in the art for techniques utilizing the connection for therapeutic purposes.

SUMMARY

Embodiments of the present invention comprise a method and apparatus that captures the audio emissions of at least one ear of a patient, determines a frequency spectrum of the audio emissions, identifies a peak frequency in the frequency spectrum and produces at least one audio signal in response the peak frequency. The patient then will be able to produce this audio signal or tone with their voice in a specific way to create vibrational resonance within their body allowing the body to balance their Voice-Ear-Brain Connection and support them with a process for self-healing. This device capitalizes on the fact that the spontaneous otoacoustic emissions (SOAEs) have a bodily purpose of determining what frequencies the body needs to self-heal.

BRIEF DESCRIPTION OF THE INVENTION

So that the manner in which the above recited features of the present invention can be understood in detail, a more particular description of the invention may be had by reference to embodiments, some of which are illustrated by the appended drawings. It is noted, however, that the appended drawings illustrate only typical embodiments of this invention and are therefore not to be considered limiting of its scope, for the invention may admit to other equally effective embodiments.

DETAILED DESCRIPTION

Figure 1:
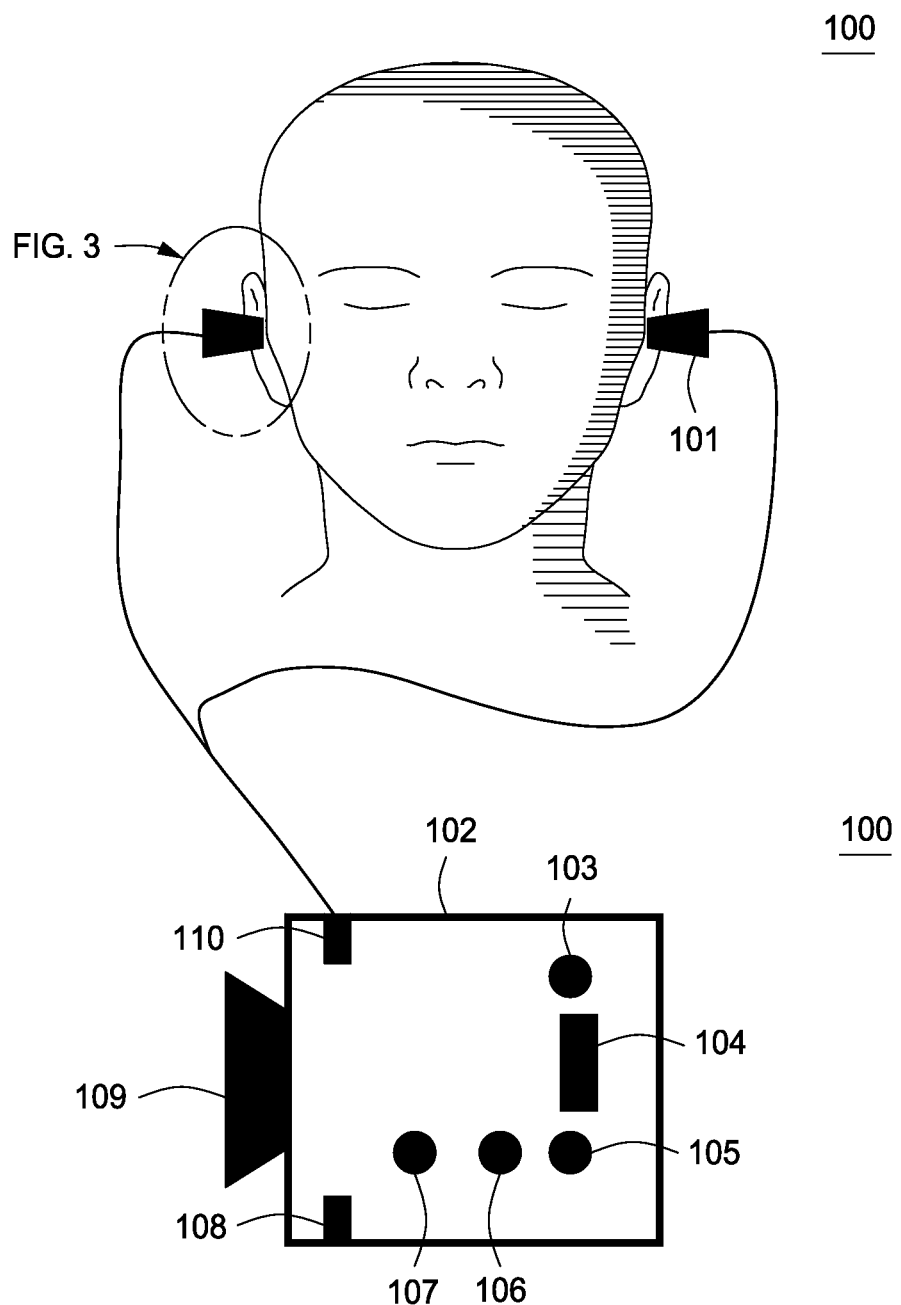
FIG. 1 is a schematic diagram of an apparatus (referred to herein as an Ototoner device) in accordance with one embodiment of the invention.

FIG. 1 depicts an apparatus (referred to herein as an Ototoner device 100) for providing therapy using spontaneous otoacoustic emission (SOAE) analysis in accordance with one embodiment of the invention. The Ototoner device 100 includes at least one microphone 101, an integrator box 102, and a speaker 109. The at least one microphone (two are shown) is placed in each ear surrounded by a cushioned sound absorbing substance. The microphones respond to (pick up) the SOAEs from the ear. The device is turned on by a power switch 104. An LED (light-emitting diode) 103 indicates that the unit is on. When the Record and Play button 105 is pressed on the integrator box 102, the integrator box 102 records the SOAEs picked up by the microphones 101 for a period of time, e.g., thirty-eight (38) seconds.

The integrator box 102 digitizes an analog audio signal, records the digital audio signal and analyzes the digital audio signal to determine a frequency with the largest amplitude (referred to herein as the peak frequency) from all of the sound collected and analyzed. The Integrator Box 102 comprises an audio synthesizer for generating an audio signal in response to the peak frequency. In one embodiment, the synthesizer generates a single frequency sine wave having the same frequency of the peak frequency and played for a period of time, e.g., 5 seconds. The sound is emitted by the speaker 109.

If the sound needs to be repeated, a Replay button 106 is depressed and the sound is replayed. This sound can continue to be replayed with the Replay button 106 until a new sound is captured through the recording function. When the Octave Harmonizer button 107 is pressed, audio signal in the form a sound is emitted which includes the peak frequency initially emitted within other octaves of that frequency that are in harmony with the original peak frequency.

In some embodiments, each ear will have the microphone 101, specifications of which are negative forty-five (−45) dB at twenty (20) Hz to five (5) KHz. surrounded by a cushioned insert earplug which is attached to a cord that connects in a Y cord traveling into the input port 110 of the integrator box 102. The microphones 101 are to be inserted into the ear canals of both ears, one to each ear.

The integrator box 102 takes the input from the two microphones 101, analyzes it, and emits a sound from the speaker 109 in response to the analysis as explained further below. The integrator box 102 may be a standalone unit (desktop or handheld) or a computer such as a desktop computer, laptop computer, and the like. Also, the integrator box 102 functions could be included as an application program in any computing device including cellular telephones, personal digital assistants, digital music players, and the like.

The power light 103 is an LED that is solidly illuminated when the power is on and flashes when the sound is being captured by the microphones 101. The LED remains solidly illuminated after the sound is analyzed indicating that the power is still on and no more analysis is being performed. If the unit is turned off, the LED is not illuminated. The power switch 104 turns the power on and off.

The Record and Play button 105 is depressed to initiate the simultaneous recording of the spontaneous otoacoustic emissions from both ears. Various software modules within the Integrator box 102 process the audio input from the microphones 101 to determine the peak frequency of the input source. The input signal is filtered to allow only frequencies between 65 to 650 Hz to be analyzed. A Fast Fourier Transform (FFT) is performed on the input to determine the peak frequencies. The frequency with the greatest amplitude (i.e., the peak frequency) is then determined. Once determined, a sound having the same frequency as the peak frequency is synthesized and sent to the digital to analog converter (DAC). The DAC applies an analog audio signal to the speaker and the speaker produces the sound for a period of time, for example, 5 seconds. The Replay button 106 can be pressed to repeat the sound (i.e., audio signal) for another five (5) seconds. This will continue each time the Replay button 106 is pressed until the unit is turned off and/or the Record and Play button 105 is pressed to begin recording a new sound.

The octave harmonizer button 107 activates an ISO226 Equal Loudness contour audio signal which includes other octaves that are in harmony with the peak frequency. Such an audio signal may be emitted as a sound and can be utilized for identifying which sound to vocally produce for therapeutic purposes. When the Octave Harmonizer Button 107 is pressed, the sound will be emitted in which an audio signal having the peak frequency is initially emitted within other octaves having frequencies that are in harmony with the peak frequency.

The power input 108 is a power source, for example, a 12 Volt 1.5 Amp power supply. The power supply may be internal or external (power adapter) to the Integrator Box. The power source may also include one or more batteries. The speaker 109 is, for example, an eight (8) Ohm five (5) Watt speaker. The microphone Input 110 connects the microphones 101 via Y cord to the Integrator Box 102.

Figure 2:
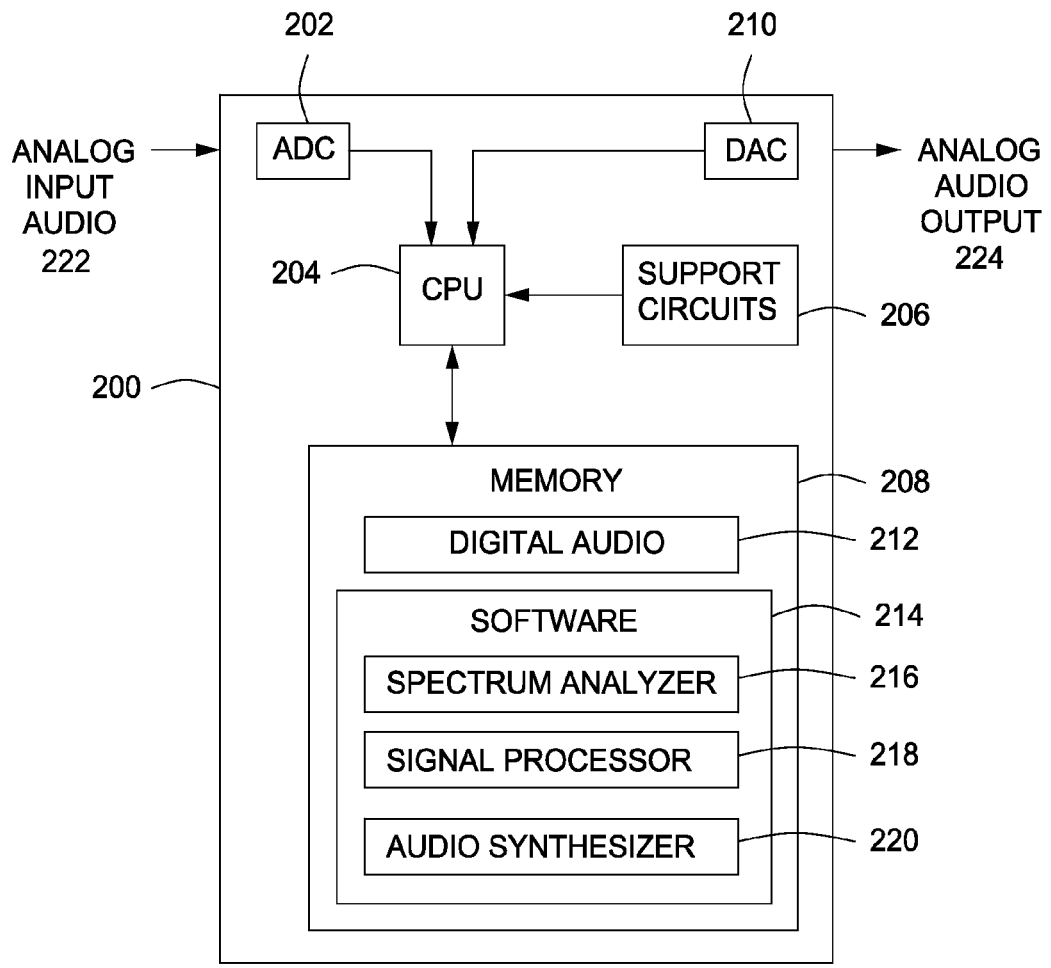
FIG. 2 is a block diagram of a computer for an integrator box in accordance with one embodiment of the invention.

FIG. 2 is a block diagram of a computer 200 according to one or more embodiments. The computer 200 may form an integration unit (e.g., the integrator box 102 of FIG. 1) of an Ototoner device (e.g., the Ototoner device 100 of FIG. 1). The computer 200 comprises an analog-to-digital converter (ADC) 202, a central processing unit (CPU) 204, support circuits 206, memory 208, and a digital-to-analog converter (DAC) 210. These components may be part of a standalone device that is purpose built to perform the functions of the Ototoner Device, or the components may be part of a general purpose computing device or system such as a laptop computer, desktop computer, notebook computer, electronic pad, digital music player, cellular telephone, personal digital assistant, and the like.

The computer 200, when executing software 214 as described below, utilizes a voice-ear-brain connection to achieve self-healing for a patient. The ADC 202 converts analog input audio 222 from the ear microphones into digital audio 212. The digital signals are applied to the CPU 204. The CPU 204 comprises one or more of any commercially available microprocessor or microcontroller that can be programmed to perform the processed described herein. The support circuits 206 comprise well known circuits that facilitate functionality of the CPU 204. Such circuits 206 may include, but are not limited to, clock circuits, cache, power suppliers, interface circuitry and so on. The memory 208 comprises forms of storage for digital information such as random access memory, read only memory, disk drives, and so on. The memory 208 comprises processor-executable instructions in the form of the software 214 that when executed by the CPU 204 causes the CPU 204 to perform various method steps.

The software 214 (execution of which is discussed in detail below with respect to FIG. 4) comprises a spectrum analyzer 216, a signal processor 218, and an audio synthesizer 220. As the ADC 202 produces the digital audio 212, the CPU 204 stores the digital audio signals in memory 208 as a file or other retrieval digital storage element. The spectrum analyzer 216 processes the input audio 212 to determine the frequency spectrum of the SOAEs. The signal processor 218 processes the spectrum to determine a peak frequency. Peak frequency information is coupled to the audio synthesizer 220. The audio synthesizer 220 produces an audio signal corresponding to the peak frequency. In one embodiment, the audio synthesizer 220 either produces one or more audio signals having the frequency of the peak frequency or produces a frequency contour (e.g., ISO 226 Equal Loudness Contour). The DAC 210 converts the audio synthesizer output into an analog signal for the speaker to form the analog audio output 224.

Figure 3:
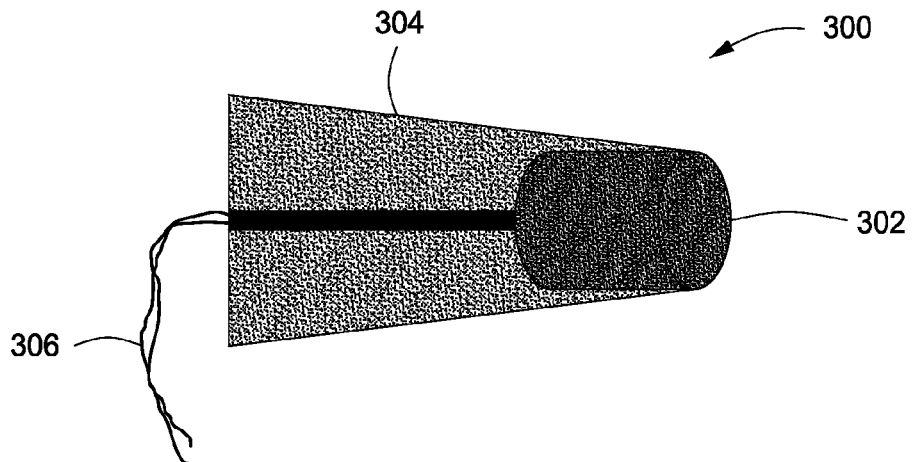
FIG. 3 is an perspective view of an ear microphone used as part of the apparatus of FIG. 1.

FIG. 3 illustrates an ear-microphone 300 for an Ototoner device according to one or more embodiments. In some embodiments, the ear-microphone 300 is one of a pair of ear-microphones. The ear microphone 300 is, for example, an audio transducer 302 covered with cushioning foam 304 to enable the audio transducer 302 to be fit tightly, but comfortably, into an ear canal. Wires 306 enable transmission of audio signals between the ear canal and an integration unit (e.g., the integrator box 102 of FIG. 1).

Figure 4:
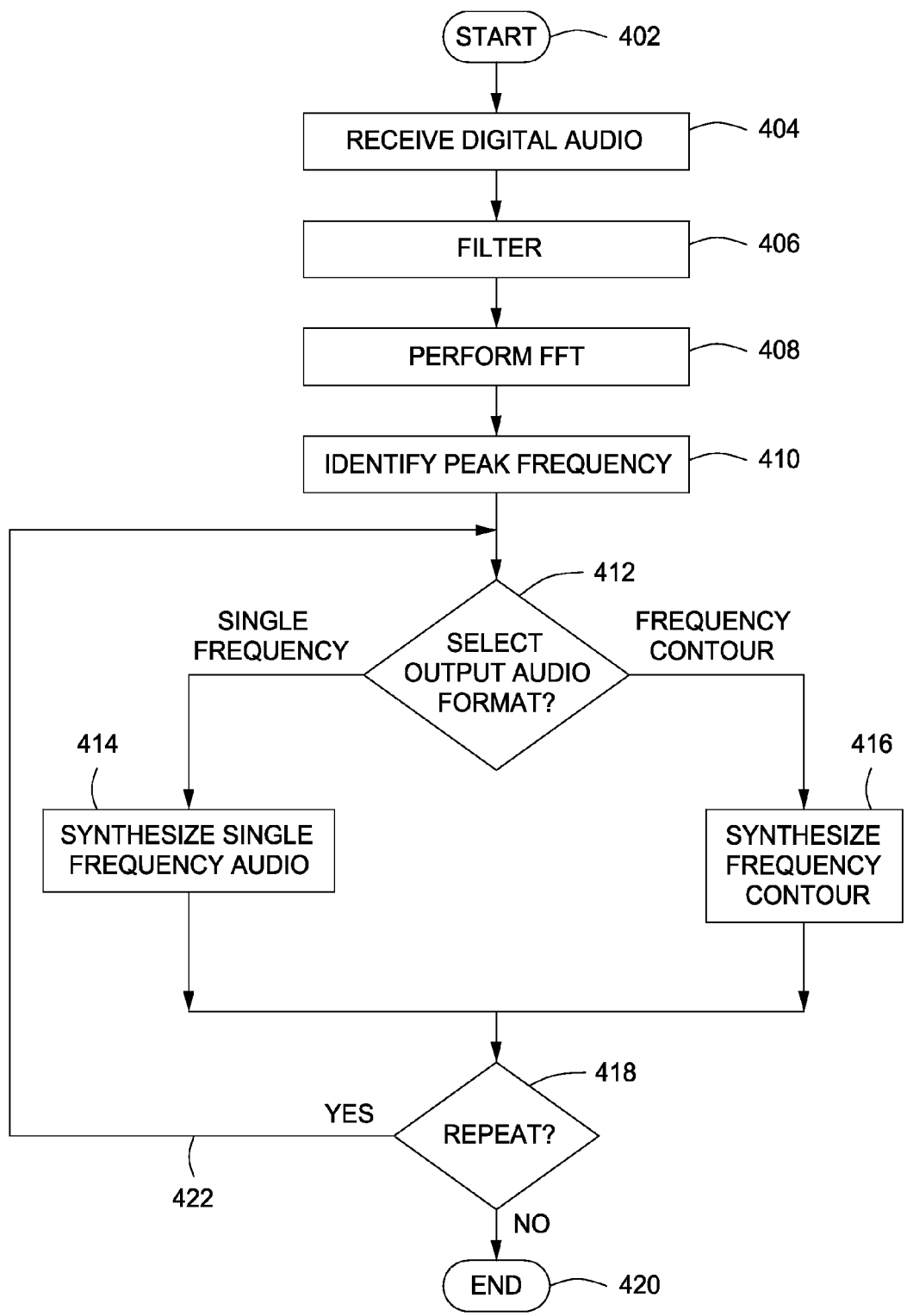
FIG. 4 is a flow diagram of a method performed by the apparatus of FIG. 1 in accordance with one embodiment of the invention.

FIG. 4 is a flow diagram of a method 400 for utilizing the voice-ear-brain connection to achieve self-healing. In some embodiments, each and every step of the method 400 is performed using processor-executable instructions (e.g., the software 214 of FIG. 2) that are stored in memory (e.g., the memory 208 of FIG. 2) and executed by a processor (e.g., the CPU 204 of FIG. 2). The method 400 begins at step 402 and proceeds to step 404, where a digital audio signal is received directly from the ADC or is recalled from memory. At step 406, the method 400 filters the digital audio signal to limit a frequency band to a particular range, for example, sixty-five (65) Hz to six hundred and fifty (650) Hz. In one embodiment, filtering is performed using a digital filter implemented in software (e.g., the software 214 of FIG. 2). The filtering process may also be performed prior to the ADC using an analog filter or within the ADC itself using a digital filter.

At step 408, the method 400 performs a Fast Fourier Transform (FFT) on the filtered audio, which results in a representation of a frequency spectrum of SOAEs associated with a patient's ear. At step 410, the method 400 identifies the frequency within the spectrum having the largest amplitude, i.e., the peak frequency. Peak frequency identification may be performed using a well-known thresholding technique. At step 412, the method 400 determines which output audio format to use for producing one or more audio signals in response to the peak frequency. If the output audio format is selected to be a single frequency, the method 400 proceeds to step 414. At step 414, the method 400 synthesizes a single frequency audio signal having the peak frequency. Alternatively, if the audio format is selected to be a frequency contour, the method 400 proceeds to step 416. At step 416, the method synthesizes a frequency contour, e.g., ISO226 Equal Loudness contour. The resulting audio signal is synthesized for a period of time, e.g., five (5) seconds.

At step 418, the method 400 queries whether a Replay button (e.g., the Replay button 106 of FIG. 1) is depressed. If the query is affirmatively answered, the method 400 proceeds along path 422 to step 412 to replay the designated audio format. In some embodiments, the method 400 repeats a sound in the form of either the single frequency audio signal or the synthesized frequency contour. If the synthesized frequency contour is repeated, a sound is produced in which other octaves are included along with an audio signal having the peak frequency. Such a sound may be emitted through a speaker associated with an integration unit (e.g., the integrator box 102 of FIG. 1). If the query at step 418 is negatively answered, the method 400 proceeds to step 420 and ends.

The embodiments of the invention described herein provide a method and apparatus for capturing SOAEs, analyzing the SOAEs, synthesizing a therapeutic audio signal derived from the analysis, and playing the audio signal as an audible sound to be used by a patient during bioacoustic therapy.

While the foregoing is directed to embodiments of the present invention, other and further embodiments of the invention may be devised without departing from the basic scope thereof.

The invention claimed is:

1. A method for utilizing the voice-ear-brain connection to achieve self-healing, comprising:
   capturing spontaneous otoacoustic emissions (SOAEs) of at least one ear of a patient;
   determining a frequency spectrum of the spontaneous otoacoustic emissions;
   identifying a peak frequency in the frequency spectrum;
   producing at least one audio signal in response to the peak frequency, wherein the at least one audio signal comprises at least one of the peak frequency or an octave in harmony with the peak frequency; and
   applying the at least one audio signal to the at least one ear of the patient as an audible sound for use by the patient to vocally reproduce at least part of the audible sound during bioacoustic therapy.

2. The method of claim 1, further comprising:
   processing an analog audio signal that is formed using the spontaneous otoacoustic emissions;
   recording a digital audio signal representing the analog audio signal; and
   determining a frequency having a largest amplitude, wherein the frequency having the largest amplitude is the peak frequency.

3. The method of claim 1, wherein the at least one audio signal is emitted as the audible sound through a speaker.

4. The method of claim 3 further comprising repeating the audible sound.

5. The method of claim 1 further comprising producing a frequency contour that comprises octaves in harmony with the peak frequency.

6. The method of claim 1 wherein the audible sound comprises the peak frequency emitted within octaves having frequencies that are in harmony with the peak frequency.

7. An Ototoner device for utilizing the voice-ear-brain connection for self-healing, comprising:
   an integration unit coupled to at least one ear-microphone and configured to capture spontaneous otoacoustic emissions (SOAEs) of at least one ear of a patient, comprising:
   a filter for filtering the spontaneous otoacoustic emissions to allow frequencies between 65 to 650 Hz;
   a spectrum analyzer for determining a frequency spectrum of the filtered spontaneous otoacoustic emissions;
   a signal processor for identifying a peak frequency in the frequency spectrum; and
   an audio synthesizer for producing at least one audio signal, in response to the peak frequency, for being applied to the at least one ear of the patient as an audible sound for use by the patient to vocally reproduce at least part of the audible sound during bioacoustic therapy, wherein the at least one audio signal comprises at least one of the peak frequency or an octave in harmony with the peak frequency, and wherein the Ototoner device is a bioacoustic feedback device.

8. The Ototoner device of claim 7, wherein the spontaneous otoacoustic emissions form an analog audio signal, further comprising:
   an analog to digital convertor for digitizing the analog audio signal; and
   a memory for storing the digitized audio signal.

9. The Ototoner device of claim 7, wherein the audio synthesizer is coupled to a speaker for emitting the at least one audio signal as the audible sound having the peak frequency.

10. The Ototoner device of claim 9, wherein the audio synthesizer is further configured to repeat the audible sound.

11. The Ototoner device of claim 7, wherein the audio synthesizer is further configured to produce a frequency contour that comprises octaves in harmony with the peak frequency.

12. The Ototoner device of claim 7, wherein the audio synthesizer is further configured to produce the audible sound having the peak frequency emitted within octaves having frequencies that are in harmony with the peak frequency.

13. A non-transitory computer readable medium storing processor executable instructions that, when executed by a computing device, cause the computing device to perform a method comprising:
- capturing spontaneous otoacoustic emissions (SOAEs) of at least one ear of a patient;
- determining a frequency spectrum of the spontaneous otoacoustic emissions;
- identifying a peak frequency in the frequency spectrum; and
- producing at least one audio signal, in response to the peak frequency, for being applied to the at least one ear of the patient as an audible sound for use by the patient to vocally reproduce at least part of the audible sound during bioacoustic therapy, wherein the at least one audio signal comprises at least one of the peak frequency or an octave in harmony with the peak frequency.

14. The non-transitory computer readable medium of claim 13 further comprising processor executable instructions that, when executed by the computing device, cause the computing device to perform the method further comprising:
- processing an analog audio signal that is formed by the spontaneous otoacoustic emissions;
- digitizing the analog audio signal into a digital audio signal; and
- storing the digital audio signal in a memory.

15. The non-transitory computer readable medium of claim 13 further comprising processor executable instructions that, when executed by the computing device, cause the computing device to perform the method further comprising:
- emitting the at least one audio signal as the audible sound through a speaker.

16. The non-transitory computer readable medium of claim 15 further comprising processor executable instructions that, when executed by the computing device, cause the computing device to perform the method further comprising:
- repeating the audible sound.

17. The non-transitory computer readable medium of claim 13 further comprising processor executable instructions that, when executed by the computing device, cause the computing device to perform the method further comprising:
- producing a frequency contour that comprises octaves in harmony with the peak frequency.

18. The non-transitory computer readable medium of claim 13 further comprising processor executable instructions that, when executed by the computing device, cause the computing device to perform the method further comprising:
- producing the audible sound having the peak frequency emitted within octaves having frequencies that are in harmony with the peak frequency.

* * * * *